United States Patent [19]

Schoemans et al.

[11] 4,312,811
[45] Jan. 26, 1982

[54] PROCESS FOR THE PRODUCTION OF SUBSTITUTED ANTHRAQUINONES

[75] Inventors: Jean Schoemans; Edmond Bouillet, both of Brussels, Belgium

[73] Assignee: Interox (Société Anonyme), Brussels, Belgium

[21] Appl. No.: 183,826

[22] Filed: Sep. 3, 1980

[30] Foreign Application Priority Data

Sep. 13, 1979 [FR] France .............................. 79 23065

[51] Int. Cl.$^3$ ............................................. C07C 58/18
[52] U.S. Cl. ................................................... 260/369
[58] Field of Search ......................................... 260/369

[56] References Cited

U.S. PATENT DOCUMENTS

| | | | |
|---|---|---|---|
| 3,032,560 | 5/1962 | Dawsey | 260/369 |
| 4,045,456 | 8/1977 | Merger et al. | 260/369 |
| 4,087,458 | 5/1978 | Emori et al. | 260/369 |

FOREIGN PATENT DOCUMENTS 52-25762  2/1977  Japan .................................. 260/369

Primary Examiner—Winston A. Douglas
Assistant Examiner—Raymond K. Covington
Attorney, Agent, or Firm—Spencer & Kaye

[57] ABSTRACT

Substituted anthraquinones are obtained by thermal or catalytic dehydrochlorination of the corresponding substituted ortho-benzoylbenzoic acid chloride.

They may be used for the production of hydrogen peroxide and the synthesis of dyes.

14 Claims, No Drawings

PROCESS FOR THE PRODUCTION OF SUBSTITUTED ANTHRAQUINONES

BACKGROUND OF THE INVENTION

The present invention relates to a new process for the production of substituted anthraquinones which are used as synthesis intermediaries, notably for the production of hydrogen peroxide and the synthesis of dyes.

It is known to produce substituted anthraquinones by dehydrating the corresponding benzylbenzoic acids using oleum (U.S. Pat. No. 3,032,560 filed on May 29, 1959 in the name of L. H. Dawsey). These processes require the use of large quantities of oleum, which leads to the formation of residual sulphuric acid contaminated by organic substances which is very difficult to recover.

There have also been attempts to prepare unsubstituted anthraquinone by a direct reaction between phthaloyl chloride and benzene (C. Friedel and J. M. Crafts, Ann. Chim. Phys., 1884, (6), 1, page 5230). The main product of this reaction is, however, a phenylphthalide, anthraquinone being produced only in traces.

SUMMARY OF THE INVENTION

The present invention aims to provide a process for the production of substituted anthraquinones which makes it possible to prevent the formation of residual sulphuric acid. The process, which is simple to carry out, enables good yields and a good selectivity to be obtained because it does not give rise to the formation of excessive quantities of phenylphthalides.

To this end, the invention relates to a process for the production of substituted anthraquinones according to which the corresponding substituted ortho-benzoylbenzoic acid chloride is dehydrochlorinated.

DETAILED DESCRIPTION OF THE INVENTION

The process according to the invention can be applied to the production of various types of substituted anthraquinones. More particularly, it is suitable for the production of anthraquinones having the formula

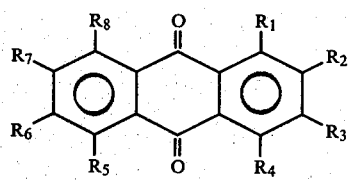
(I)

where the substituents $R_1$, $R_2$, $R_3$, $R_4$, $R_5$, $R_6$, $R_7$ and $R_8$ represent a hydrogen atom or a carbon-containing group containing 1–12 carbon atoms, $R_1$, $R_2$, $R_3$, $R_4$, $R_5$, Rhd 6, $R_7$ and $R_8$ being the same or different, at least one of these substituents representing a carbon-containing group.

According to the invention, these anthraquinones are obtained by cyclisation of the corresponding acid chloride having the formula

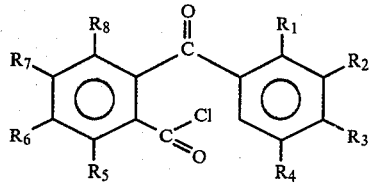
(II)

where the substituents have the same meaning as above. These acid chlorides can be produced according to the process described in applicants' copening U.S. application Ser. No. 183,824, equivalent to a French patent application filed by the Applicants on the same day as the present priority application.

The above-mentioned carbon-containing groups can be of various kinds; they can be made up of groups chosen from the alkyl, alkenyl, aryl, alkylaryl, alkenylaryl, aralkyl, aralkenyl, cycloalkyl and cycloalkenyl groups. In pairs ($R_1$-$R_2$, $R_2$-$R_3$, $R_3$-$R_4$, $R_5$-$R_6$, $R_6$-$R_7$ and/or $R_7$-$R_8$) they may also constitute one or more single carbon-containing chains. The carbon-containing groups may possibly contain in their structure hetero atoms such as halogens, oxygen, nitrogen or sulphur.

The process according to the invention is quite suitable for the production of substituted anthraquinones of formula I where the substituents $R_5$ and $R_7$ both represent a hydrogen atom. It is particularly suitable for the production of substituted anthraquinones of formula I where the substituents $R_2$, $R_4$, $R_5$ and $R_7$ all represent a hydrogen atom.

The process according to the invention is quite suitable for the production of substituted anthraquinones of formula I where the substituent $R_3$ represents a carbon-containing group containing at least 2 carbon atoms and preferably an alkyl group containing 2 to 8 carbon atoms. The best results were obtained with anthraquinones whose substituents $R_1$, $R_2$, $R_4$, $R_5$, $R_6$, $R_7$ and $R_8$ represent hydrogen and substituent $R_3$ represents an alkyl group containing 2 to 8 carbon atoms. 2-Ethylanthraquinone, 2-propyl-and 2-isopropyl-anthraquinones, 2-butyl-, 2-tert.butyl-, 2-isobutyl-anthraquinones and 2-pentyl-, 2-sec.amyl- and 2-tert.amyl-anthraquinones can be mentioned as examples of such substituted anthraquinones.

Dehydrochlorination can take place in the presence or absence of a specially added catalyst.

Catalysts of the Friedel Crafts type are generally used as a catalyst for the reaction. Examples of these catalysts are given in the book Friedel-Crafts and Related Reactions by G. A. Olah, Volume I, 1963, Interscience Publ. It is thus possible to use Bronsted acids or Lewis acids. Hydrogen chloride or non-protonic Lewis acids are most often used. Of these, the halides and more particularly the metal chlorides are quite suitable. Good results have been obtained with aluminium chloride. It is also possible to use mixtures of catalysts.

These catalysts are generally used in relatively large quantities. A quantity of 0.01 to 20 mole of catalyst per mole of acid chloride is most often used. Good results have been obtained using 1–5 mole of catalyst per mole of acid chloride.

The reaction is generally carried out in the liquid phase. It may take place in the presence or absence of a solvent. The solvents used are chosen from the solvents which are inert under the reaction conditions. It is preferable to choose solvents capable of solubilising the acid chloride and, as the case may be, the catalyst used. It is possible to use one solvent or a mixture of solvents.

The solvents are generally chosen from sulphur dioxide and substituted or unsubstituted hydrocarbons. These hydrocarbons generally contain 1 to 12 and preferably 1 to 8 carbon atoms. They can be of various types and can contain groups such as alkyl, alkenyl, cycloalkyl, cycloalkenyl, aryl, aralkyl, aralkenyl, alkylaryl and alkenylaryl and heterocyclic groups. Their potential substituents can be of very different kinds; they are generally chosen from halogen atoms or sulphur atoms and the nitro, sulphone sulphoxide, ether and thioether groups.

Halogenated hydrocarbons and more particularly chlorinated hydrocarbons, more particularly those which contain 1 to 7 carbon atoms, and carbon disulphide are quite suitable. Good results have been obtained with carbon disulphide, tetrachloromethane, trichloromethane, dichloromethane, 1,2-dichloroethane, 1,2-dichloroethylene, trichlorethylene and perchloroethylene.

The potential solvents can also be used in varying quantities. The reaction mixture generally contains up to 95% by weight of solvent.

The reaction temperature can vary within wide limits. It is generally between 300 and 600 K. The reaction pressure can also vary within wide limits. The reaction pressure is generally chosen in such a way as to maintain the reaction mixture in liquid form. The pressure is most often between 0.1 and 100 bar.

If dehydrochlorination is carried out in the presence of catalyst, a solvent such as defined above is generally used. In this case, the reaction mixture usually contains 30 to 95% by weight of solvent. Good results have been obtained using reaction mixtures containing 50 to 90% by weight of solvent. In the presence of catalysts, the temperature chosen is generally below 400 K. Most often it is between 300 and 370 K. The pressure is then generally between 0.1 and 5 bar.

If dehydrochlorination is carried out largely in the absence of an external catalyst (i.e. in the presence of less than 0.1 mole of catalyst such as defined above, per mole of acid chloride), reaction temperatures above 350 K are generally used. Most often, temperatures between 370 and 600 K are used. Good results have been obtained using temperatures between 400 and 550 K. In this case, the pressure is generally between 0.8 and 100 bar and most often between 1 and 80 bar.

When operating in the absence of external catalyst, it is probable that the reaction is catalysed by the hydrogen chloride produced by the reaction.

As mentioned above, the reaction in the presence or absence of external catalyst is generally carried out in a liquid medium. This medium may possibly be kept at boiling point. The reaction can be conducted in reactors under a partial vacuum or in reactors capable of operating under high pressure depending on the reaction pressures. The reactors used are generally made of materials capable of resisting corrosion.

The reaction can take place continuously or discontinuously in a single reactor or in reactors in stages.

In order to illustrate the invention yet without limiting its scope, examples of the production of substituted anthraquinones are given below. Examples 1, 2, 3, 4, 6, 7, 8, 9, 10 and 11 were carried out in the presence of a catalyst, examples 5 and 12 were carried out in the absence of a specially added catalyst.

Production of 2-ethylanthraquinone vcl Example 1

A 20% by weight solution of ortho(4'-ethylbenzoyl)-benzoic acid chloride (purity 94%) in 1,2-dichloroethane is used. The solution is kept at 288 K and 3 moles of aluminum chloride per mole of acid chloride are introduced over a period of 1 hour 20 minutes.

The mixture is brought to 303 K and is kept at this temperature for 4 hours. 2-Ethylanthraquinone is obtained with a yield of 39.9% and a selectivity of 81%.

Production of a mixture of 2-sec- and 2-tert-amylanthraquinones(ratio of the two isomers approx. 1:1)

Example 2

A 20% by weight solution of a mixture of ortho-(4'-sec-and 4'-tert-amylbenzoyl)benzoic acid chlorides (purity 92%) in 1,2-dichloroethane is used. A quantity of 3 moles of aluminum chloride per mode of acid chloride is introduced into the solution over a period of 1 hour 20 minutes.

The mixture is brought to 323 K and is kept at this temperature for 5 hours.

A mixture of 2-sec- and 2-tert-amylanthraquinones is obtained with a yield of 87.3% and a selectivity of 94%.

Example 3

A 20% by weight solution of a mixture of ortho-(4'-sec- and 4'-tert-amylbenzoyl)benzoic acid chlorides in carbon disulphide is used and the procedure as in example 2 is followed.

After 3 hours 30 minutes reaction at 313 K, a mixture of 2-sec- and 2-tert-amylanthraquinones is obtained with a yield of 79% and a selectivity of 84%.

Example 4

A 20% by weight solution of a mixture of ortho-(4'-sec- and 4'-tert-amylbenzoyl)benzoic acid chlorides in tetrachloromethane is used and the procedure as in Example 2 is followed. After 3 hours 30 minutes reaction at 323 K, a mixture of 2-sec- and 2-tert-amylanthraquinones is obtained with a yield of 70% and a selectivity of 84%.

Example 5

A quantity of 50 g of a mixture of ortho-(4'-sec- and 4'-tert-amylbenzoyl)benzoic acid chorides is placed in an autoclave made of stainless steel kept at a pressure of 20 bar under a nitrogen atmosphere. The temperature is kept at 498 K.

A mixture of 2-sec- and 2-tert-amylanthraquinones is obtained with a yield of 55.3% and a selectivity of 80%.

Production of 2-tert-butylanthraquinone

Example 6

A 20% by weight solution of ortho-(4'-tert-butylbenzoyl)benzoic acid chloride in 1,2-dichloroethane is used. A quantity of 3.09 moles of aluminium chloride per mole of acid chloride is introduced into the solution over a period of 1 hour 20 minutes.

The mixture is brought to 313 K and is kept at this temperature for 5 hours.

2-Tert-butylanthraquinone is obtained with a yield of 91.6% and a selectivity of 97%.

Example 7

A 20% by weight solution of ortho-(4'-tert-butylbenzoyl)benzoic acid chloride in dichloromethane is used. A quantity of 3.09 moles of aluminium chloride per mole of acid chloride is introduced into the solution over a period of 1 hour 20 minutes.

The mixture is brought to 308 K and is kept at this temperature for 6 hours.

2-Tert-butylanthraquinone is obtained with a yield of 79.1% and a selectivity of about 100%.

Example 8

The procedure as in Example 7 is followed using 1,2-dichloroethylene as a solvent and a reaction temperature of 313 K.

2-Tert-butylanthraquinone is obtained with a yield of 79.1% and a selectivity of about 100%.

Example 9

The procedure as in Example 7 is followed using perchloroethylene as a solvent and a temperature of 323 K.

2-Tert-butylanthraquinone is obtained with a yield of 81.5% and a selectivity of 85%.

Example 10

The procedure as in Example 7 is followed using carbon tetrachloride as a solvent and a temperature of 323 K.

2-Tert-butylanthraquinone is obtained with a yield of 90.3% and a selectivity of 97%.

Example 11

The procedure as in Example 7 is followed using carbon disulphide as a solvent and temperature of 313 K.

2-Tert-butylanthraquinone is obtained with a yield of 93.3% and a selectivity of about 100%.

Example 12

A quantity of 90 g of ortho-(4'-tert-butylbenzoyl)benzoic acid chloride is placed in an autoclave made of stainless steel kept under a pressure of 20 bar under a nitrogen atmosphere. The temperature is kept at 473 K.

2-Tert-butylanthraquinone is obtained with a yield of 85.6% and a selectivity of 97%.

What is claimed is:

1. Process for the production of substituted anthraquinones comprising dehydrochlorinating the corresponding substituted ortho-benzoylbenzoic acid chloride.

2. Process according to claim 1, wherein said anthraquinones have the formula

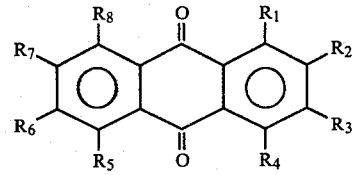

where the substituents $R_1$, $R_2$, $R_3$, $R_4$, $R_5$, $R_6$, $R_7$ and $R_8$ represent a hydrogen atom or a carbon-containing group containing 1 to 12 carbon atoms, where $R_1$, $R_2$, $R_3$, $R_4$, $R_5$, $R_6$, $R_7$ and $R_8$ can be the same or different, at least one of these substituents representing a carbon-containing group, and said corresponding acid chlorides have the formula

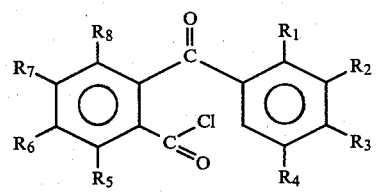

where $R_1$, $R_2$, $R_3$, $R_4$, $R_5$, $R_6$, $R_7$ and $R_8$ have the same meaning.

3. Process according to claim 2, wherein $R_2$, $R_4$, $R_5$ and $R_7$ each represents a hydrogen atom.

4. Process according to claim 3, wherein $R_1$, $R_6$ and $R_8$ each represents a hydrogen atom.

5. Process according to claim 2, 3 or 4, wherein $R_3$ represents an alkyl group containing 2 to 8 carbon atoms.

6. Process according to claim 1, 2, 3 or 4, weherein said dehydrochlorinating is carried out in the presence of a catalyst of the Friedel-Crafts type.

7. Process according to claim 6, wherien said catalyst comprises chloride.

8. Process according to claim 1, 2, 3, or 4, wherein said dehydrochlorinating is carried out in the presence of a solvent.

9. Process according to claim 8, wherein the solvent is selected from the group consisting of carbon disulphide and chlorinated hydrocarbons containing 1 to 7 carbon atoms.

10. Process according to claim 6 wherein said dehydrochlorinating is carried out at a temperature between 300 and 370 K.

11. Process according to claim 1, 2, 3 or 4, wherein said dehydrochlorinting is carried out at a temperature between 400 and 550 K in the presence of less than 0.1 mole of catalyst per mole of acid chloride.

12. Process according to claim 7, wherein said dehydrochlorinating is carried out at a temperature between 300 and 370 K.

13. Process according to claim 8, wherein dehydrochlorinating is carried out at a temperature between 400 and 550 K in the presence of less than 0.1 mole of catalyst per mole of acid chloride.

14. Process according to claim 9, wherein said dehydrochlorinating is carried out at a temperature between 400 and 550 K in the presence of less than 0.1 mole of catalyst per mole of acid chloride.

* * * * *